United States Patent
Sato et al.

(10) Patent No.: US 9,079,845 B2
(45) Date of Patent: Jul. 14, 2015

(54) PROCESS FOR OBTAINING FATTY ACID ALKYL ESTERS, ROSIN ACIDS AND STEROLS FROM CRUDE TALL OIL

(75) Inventors: Setsuo Sato, Jacareí (BR); Henrique Jorge Sousa Sales, São José dos Campos (BR); Hercules Peloggia, Jacareí (BR); Peter Kempers, Grevenbroich (DE); Sabine Both, Neuss (DE); Ulrich Schoerken, Duesseldorf (DE); Thomas Wolf, Haan (DE)

(73) Assignee: Cognis IP Management GmbH, Duesseldorf (DE)

( * ) Notice: Subject to any disclaimer, the term of this patent is extended or adjusted under 35 U.S.C. 154(b) by 1874 days.

(21) Appl. No.: 10/546,426

(22) PCT Filed: Feb. 20, 2004

(86) PCT No.: PCT/BR2004/000016
§ 371 (c)(1),
(2), (4) Date: Feb. 17, 2006

(87) PCT Pub. No.: WO2004/080942
PCT Pub. Date: Sep. 23, 2004

(65) Prior Publication Data
US 2006/0235198 A1 Oct. 19, 2006

(30) Foreign Application Priority Data
Feb. 21, 2003 (WO) ................ PCT/BR03/00024

(51) Int. Cl.
| | | |
|---|---|---|
| C09F 7/00 | (2006.01) |
| C07J 9/00 | (2006.01) |
| C07J 51/00 | (2006.01) |
| C07C 51/43 | (2006.01) |
| C07C 51/42 | (2006.01) |
| C07C 51/44 | (2006.01) |
| C07C 67/08 | (2006.01) |
| C07C 67/54 | (2006.01) |
| C07J 75/00 | (2006.01) |
| C11B 13/00 | (2006.01) |
| C11C 1/10 | (2006.01) |
| C11C 3/00 | (2006.01) |
| C12P 7/62 | (2006.01) |
| C12P 7/64 | (2006.01) |

(52) U.S. Cl.
CPC .......... *C07C 51/42* (2013.01); *C07C 51/44* (2013.01); *C07C 67/08* (2013.01); *C07C 67/54* (2013.01); *C07J 9/00* (2013.01); *C07J 51/00* (2013.01); *C07J 75/00* (2013.01); *C11B 13/005* (2013.01); *C11C 1/10* (2013.01); *C11C 3/003* (2013.01); *C12P 7/62* (2013.01); *C12P 7/649* (2013.01); *Y02E 50/13* (2013.01)

(58) Field of Classification Search
None
See application file for complete search history.

(56) References Cited

U.S. PATENT DOCUMENTS

| | | | | |
|---|---|---|---|---|
| 2,415,301 A | * | 2/1947 | Mattikow | 536/5 |
| 3,496,159 A | * | 2/1970 | Spence | 530/207 |
| 3,804,819 A | | 4/1974 | Wengrow et al. | |
| 4,122,291 A | * | 10/1978 | Kyo et al. | 568/887 |
| 4,956,286 A | * | 9/1990 | Macrae | 435/134 |
| 5,424,457 A | * | 6/1995 | Sumner et al. | 549/408 |
| 5,627,289 A | | 5/1997 | Jeromin et al. | |
| 5,670,669 A | * | 9/1997 | Hunt | 549/413 |
| 6,107,456 A | * | 8/2000 | Huibers et al. | 530/205 |
| 6,344,573 B1 | | 2/2002 | Rohr et al. | |
| 6,413,571 B1 | * | 7/2002 | Liu | 426/611 |
| 6,414,111 B2 | | 7/2002 | Huibers et al. | |
| 6,429,320 B1 | * | 8/2002 | McCurry et al. | 549/413 |
| 2007/0015904 A1 | * | 1/2007 | Sato et al. | 530/230 |

FOREIGN PATENT DOCUMENTS

| | | |
|---|---|---|
| DE | 101 19 972 | 5/2002 |
| WO | WO 94/05650 | 3/1994 |

OTHER PUBLICATIONS

Raymond Kirk & Donald Othmer, Encyclopedia of Chemical Technology 775-79 (John Wiley & Sons, Inc. 1994) (1890).*

* cited by examiner

Primary Examiner — Ernst V Arnold
Assistant Examiner — Jianfeng Song
(74) Attorney, Agent, or Firm — Servilla Whitney LLC

(57) ABSTRACT

The disclosed invention refers to a process for obtaining fatty acid alkyl esters, rosin acids and sterols from crude tall oil (CTO), which is characterized by the following steps: (a) reacting the free fatty acids present in the CTO with lower alcohols; (b) esterifying the sterols in the CTO with boric acid or transesterifying the sterols with a catalyst; (c) separating the fatty acid lower alkyl esters and rosin acids from the remaining sterol borate esters or sterol esters of fatty acids to produce a stream of sterol esters; (d) separating the fatty acid alkyl esters from the rosin acids to produce a first stream of fatty acid alky esters and a second stream of rosin acids; and (e) converting the sterol esters into the free sterols to produce a third stream of free sterols.

20 Claims, No Drawings

PROCESS FOR OBTAINING FATTY ACID ALKYL ESTERS, ROSIN ACIDS AND STEROLS FROM CRUDE TALL OIL

CROSS-REFERENCE TO RELATED APPLICATIONS

This application claims priority under 35 USC §365 from International Application PCT/BR2004/000016, filed on Feb. 20, 2004, which claims priority from International Application PCT/BR2003/000024, filed on Feb. 21, 2003.

BACKGROUND OF THE INVENTION

1. Technical Field

The invention refers to a process for obtaining fatty acid alkyl esters, rosin acids and sterols from crude tall oil (CTO) which involves several esterification and distillation steps.

2. Background Art

The use of sterols to take control of cholesterol level in human nutrition body industry might increase a lot the demand of non-sterols. Consequently, separation process of sterols from Crude Tall Oil is highly interesting from the economical viewpoint, since this is one of the main source of sterols. Crude tall oil typically comes from the sulphate process employed in the manufacture of cellulose from wood. More particularly, the spent black liquor from the pulping process is concentrated until sodium salts (soaps) of various acids separate out and are skimmed off. The salts are acidified or decomposed with sulphuric acid so as to provide the crude tall oil.

Crude tall oil is refined mainly by vacuum distillation processes to separate the various compounds almost completely into rosin and fatty acid fractions. The current technology is based on distillation where the acids are fractionated in several columns. Using a first column to separate the more volatile fatty acids and rosin acids, from the less volatile materials, which include many of the unsaponifiable and neutral materials such as sterols and their esters. A second column is commonly designed to separate the more volatile fatty acids from the less volatile rosin acids. The tall oil fatty acids usually contain 1-5% rosin acids as by-products. This process usually ends up with a bottom that is currently called as "pitch", where sterols, heavy hydrocarbons, wax alcohols are the main substances. Commercially, only fatty and rosin acids are produced. Pitch usually is used as a fuel. Due to the high distillation temperature there is significant sterols degradation. Also the most part of the free sterols are converted into esters. Tall oil pitch is a very viscous, dark product, which is rather difficult to handle. So far, there is no economic commercial process running to extract sterols from the pitch. From the state of the art a number of processes are known describing ways to extract sterols from CTO soaps using solvents and distillation processes prior to any acid splitting process, which theoretically could avoid sterols losses. See, for example, U.S. Pat. No. 6,107,456, U.S. Pat. No. 6,414,111, and U.S. Pat. No. 6,344,573. However, these processes are characterised by a high technical effort and were not reduced into practice for economical reasons.

A method of separating sterols from crude tall oil, wherein the sterols are not destroyed in the process, would be a useful invention in the chemical preparation industry. Therefore, the objective of this invention is to find out an economic process to separate the three main crude tall oil (CTO) components, fatty acids or their esters, rosin acids, and sterols, to get these commercially valuable products.

BRIEF SUMMARY OF THE INVENTION

The present invention therefore provides a new process for obtaining fatty acid alkyl esters, rosin acids and sterols from crude tall oil (CTO), which is characterised by the following steps:

(a) reacting the free fatty acids present in the CTO with lower alcohols;

(b) esterifying the sterols in the CTO with boric acid or transesterifying with catalyst;

(c) separating the fatty acid lower alkyl esters and rosin acids from the remaining sterol borate esters or sterol esters of fatty acids to produce a stream of sterol esters;

(d) separating the fatty acid alkyl esters from the rosin acids to produce a first stream of fatty acid lower alkyl esters and a second stream of rosin acids; and (e) converting said sterol esters into the free sterols to produce a third stream rich in free sterols.

DETAILED DESCRIPTION OF THE INVENTION

In more detail, in step (a) of the process the fatty acids are converted into their respective $C_1$-$C_4$ alkyl esters, preferably into their methyl esters. The major advantage of this step lies in the low boiling point of the esters thus obtained, which makes it easy to separate them from the other fractions. This is preferably done in a single esterification step due to the selective enzymatic or chemical reaction between fatty and rosin acids, with means that usually only the fatty acids are converted into their respective esters. The esterification can be conducted by means of acidic catalysts, like for example methane sulfonic acid or Fascat® at temperatures of 120 to 150° C., or enzymes, like for example the lipase Novozym® CaLB (Novozymes A/S, Denmark) at temperatures of 20 to 60° C., depending on the activity optimum of the microorganisms. Usually, the enzymatic reaction takes a significantly longer time. The esterification can be carried out under pressure.

In step (b), boric acid ($H_3BO_3$) is added to the CTO which contains fatty acid alkyl esters, sterols and rosin acids to transform all the free sterols into sterol triesters. Sterol esters are much more stable than free sterols which leads to less degradation products, especially those due to the dehydration reaction. By this step it is possible to achieve a better separation between rosins and neutrals and to avoid the unwanted degradation of the sterols. Usually, the esterification is conducted a temperature of 200 to 230° C.

Or, Fascat®4350 (Tin based catalyst) is added to the CTO which contains fatty acid alkyl esters, sterols and rosin acids to transform all the free sterols into sterol fatty esters. Usually, the transesterification is conducted at a temperature of 230° C. for 3-4 hours.

In step (c) the fatty acid alkyl esters and rosin acids are separated from the sterol borate esters and other high molecular weight hydrocarbons, preferably by means of a short pass distillation, and more preferably by means of a wiped film evaporator. The latter process is again operated preferably at a reduced pressure of from 0.01 to 10 mmHg and a temperature of 160 to 240° C.

In step (d) the fatty acid esters are separated from the remaining rosin acids by means of distillation, short path distillation or fractionation, employing milder conditions compared to the acid distillation. The fatty acid alkyl esters, preferably fatty acid methyl esters, are thereby advantageously obtained without rosin acids contamination and leaving less fatty acids in the bottom stream. The distillation is preferably carried out by means of a wiped film evaporator which is usually conducted at a reduced pressure of 0.01 to 10 mmHg and a temperature of 190 to 240° C. and/or a subsequent column consisting of e.g. 15 steps with reflux, condensate, reboiler, known from the state of the art.

In step (e), the borate sterol esters are easily converted to the free sterols through hydrolysis or solvolysis. The preferred solvent, however, is water.

This process can also be applied to the tall oil pitch to enrich the sterols content. The borate esters step can be applied to separate tocopherols and sterols from the fatty acids portion in the soy bean vegetable oil distillate (VOD), and also to separate sterols and high molecular alcohols in the sugar cane waxes. The first stream, fatty acid methyl esters, is used to produce methyl dimerate, a raw material used to make polyamides as described in the U.S. Pat. No. 6,281,373. The second stream, the rosin acids, is used to produce adhesives and other conventional products. The sterols can be used as feed in the existent purification sterols processes. The viscosity of this stream can be decreased by adding soy bean oil during the last distillation or by reacting alcohols, $C_{12}$-$C_{18}$-saturated or unsaturated during the boric acid esterification step. The alcohols can be recovered after the hydrolysis step.

EXAMPLES

1. Comparative Example

Wiped Film Evaporator Distillation of Crude Tall Oil

This example illustrates for comparison purpose a wiped film evaporator (WFE) distillation of crude tall oil (CTO) in the same wiped film evaporator equipment used to develop the entire process, without selective enzymatic or chemical esterification of fatty acid and transforming all free sterols into sterols borate triesters.

600.0 ml/h of CTO were passed through a WFE. The CTO contained 4.7% b.w. sterol, of which only 9.0% b.w. was already present as sterol esters. The WFE was operated at 1 mm Hg, with a initial residue temperature of 190° C. The residue fraction (residue 1) leaving the bottom of the WFE represented 64.0% b.w. of the CTO feed. The residue 1 contained 38.0% b.w. rosin acids, 40.0 b.w. % of TOFA. In the second distillation, the WFE was operated at 1 mm Hg, with a initial residue 1 temperature of 240° C. The residue fraction (residue 2) leaving the bottom of the WFE represented 15.0% b.w. of the residue 1 feed. The residue 2 contained 40% b.w. rosin acids, and 6% b.w. total sterol. The sterol yield in this process was 25% b.w., which means that 75% b.w. of the sterols undergo thermal degradation or distilled off together with the rosins and fatty acids.

From this example one can see that it is not possible to separate the fatty acids from the rosin acids using short path distillation, and also the sterols recovery is too low.

Inventive Examples 2-7

These inventive examples describe the use of a selective chemical and enzymatic esterification of fatty acid from crude tall oil followed by the esterification of sterols by boric acid. The fatty acid alkyl esters, rosin acids and sterol borates are separated in accordance with the present invention, to avoid the sterol degradation in the residue fraction, and producing a high quality fatty acid ester (TOFA-Me) and rosin acids from crude tall oil.

2. Esterification Step a) Chemical esterification: 1 kg of CTO obtained from RESITEC Industrias Quimicas LTDA, were placed together with 750 g (23.43 moles) of methanol from Aldrich Chemical Co. and 12 g of methanesulfonic acid (0.12 moles) from Merck KGaA, into a 2-1-Büchi laboratory autoclave BEP 280 equipped with a thermometer, and mechanical agitator. Over a two-hour period, the temperature was maintained at 140° C. Thereafter, the temperature was reduced from 140° C. to 70° C. and the unreacted methanol distilled off. The maximum reaction pressure in the reaction was 7 bar. The acid value of the CTO was reduced from initially 154 mgKOH/g to 65 mgKOH/g.

b) Enzymatic esterification: 3 kg of CTO obtained from RESITEC Industrias Quimicas LTDA were placed together with 750 g (23.43 moles) of methanol from Aldrich Chemical Co., 120 g of water, and 1.5 g of Novozym® CaLB L from NOVOZYMES Latin America Ltda, in a 4-1-3-necked round bottom flask equipped with a thermometer, a mechanical agitator, and a condenser. The samples were shaken for 180 hrs at 30° C. The initial acid value of 154.0 mgKOH/g was reduced to 64.0 mgKOH/g.

c) Enzymatic esterification with immobilised enzyme: 50 g of CTO obtained from RESITEC Industrias Quimicas LTDA were placed together with 5.0 g (0.16 moles) of methanol from Aldrich Chemical Co. and 2.5 g polypropylene carrier MP 100 (Membrana, Germany) previously loaded with 1.25 g Novozym® CaLB L (Novozymes A/S, Denmark), in a flask. The samples were shaken for 22 hrs at 45° C. The initial acid value of 147.0 mgKOH/g was reduced to 69.2 mgKOH/g.

d) Enzymatic esterification with ethanol and immobilised enzyme: 50 g of CTO obtained from RESITEC Industrias Quimicas LTDA were placed together with 5.0 g (0.11 moles) of ethanol from Aldrich Chemical Co., 5.0 g of water and 2.5 g polypropylene carrier MP 100 (Membrana, Germany) previously loaded with 1.25 g Novozym® CaLB L (Novozymes A/S, Denmark), in a flask. The samples were shaken for 22 hrs at 45° C. The initial acid value of 147.0 mgKOH/g was reduced to 80.2 mgKOH/g.

The following experiments were carried out with chemical or enzymatic esterified crude tall oil, after removal of methanol and water by evaporation, according to example 2a-2d.

3. Esterification with Boric Acid/Transesterification with Tin Catalyst a) 1 kg of CTO esterified (by step 2) was dried at 110° C. and 40 mmHg, and 5.0 g of boric acid (0.03 moles) obtained from Aldrich Chemical Co., were placed into a 2-liter, 3-necked round bottom flask and reacted for 4 h at 220° C. to convert all the free sterols into esters.

b) 1 kg of CTO esterified (by step 2) dried at 110° C. and 40 mmHg and 0.4 g of Fascat®4350 obtained from Atofina, were placed into a 2-liter, 3-necked round bottom flask and reacted for 4 h at 230° C. to convert all the free sterols into esters.

4. Separation of Fatty Acid Alkyl Esters and Rosin Acids from Sterol Borates/Sterol Fatty Ester 1 kg of the product produced by step 3 was distilled in the WFE which was operated at 2 mm Hg, 210° C. and feed flow of 550 ml/hour. The residue 1 leaving the bottom of the WFE represented 20.0% w/w of the CTO feed. The residue 1 contained 21% w/w of sterols as esters and the top fraction 2 representing 80% w/w with no sterols having 62% of fatty acid methyl ester, 33% of rosin acids and 5% of unsaponifiable material. Thermal degradation reactions were minimal.

5. Separation of Fatty Acid Alkyl Esters from Rosin Acids 1600 g of the top fraction 2 obtained in the in the step 4 were distilled in a laboratory column distillation at 250° C. (bottom)/210° C. (top) and 2 mmHg. The top fraction 1 represented 65% w/w contained 90% of fatty acid methyl ester, 0.3% of rosin acid and 9.7% of unsaponifiable material. The bottom fraction 2 represented 35% having 90% of rosin acid and 10% of heavy components.

6. Hydrolysis of Sterol Borate Esters

To 500 g of the residue 1, obtained in the step 4, was added 200 g of purified water, and the resulting solution heated to 90° C. stirred for 1 hour. After phase separation the residue was washed two times with 50 g purified water and dried.

7. Solvolysis of Sterol Fatty Acid Esters

To 500 g of the residue 1, obtained in the step 4, was added 100 g of glycerin, heated up to 220° C. stirred for 3 hour. After this step 85% of free sterols are obtained and separated by appropriate methods.

What is claimed is:

1. A process for obtaining fatty acid alkyl esters, rosin acids and sterols from crude tall oil (CTO), consisting essentially of subjecting crude tall oil, comprising fatty acids, rosin acids and sterols, to the following steps:
   (a) esterifying said CTO with lower alcohols, wherein said fatty acids present in said CTO react selectively with the lower alcohols and removing lower alcohols and water from the esterified CTO mixture, forming a first CTO mixture comprising fatty acid lower alkyl esters;
   (b) further esterifying said first CTO mixture with boric acid by adding boric acid to the first CTO mixture to transform all free sterols into sterol borate triesters, forming a second CTO mixture comprising sterol borate triesters, which sterol borate triesters are less volatile and more thermally stable than the starting sterols;
   (c) separating said second CTO mixture into two fractions by short pass distillation, a first fraction comprising said fatty acid lower alkyl esters and said rosin acids, and a second fraction comprising said sterol borate triesters;
   (d) further separating said first fraction into fatty acid alkyl esters and rosin acids in a process consisting essentially of short pass distillation or wiped film evaporator distillation; and
   (e) converting said sterol borate triesters into the free sterols,
wherein step (a) is carried out in the liquid phase, optionally under pressure.

2. The process according to claim 1, wherein said esterification step (a) is carried out in the presence of an acid catalyst or in the presence of an enzyme catalyst.

3. The process according to claim 2, wherein said acid catalyst comprises methanesulfonic acid.

4. The process according to claim 2, wherein said esterification is conducted at a temperature in the range of 120 to 150° C., in the presence of an acid catalyst.

5. The process according to claim 2, wherein said esterification is carried out in the presence of an immobilized enzyme catalyst.

6. The process according to claim 2, wherein said esterification is carried out in the presence of an enzyme catalyst at a temperature in the range of 20 to 60° C.

7. A process for obtaining fatty acid alkyl esters, rosin acids and sterols from crude tall oil (CTO), consisting essentially of subjecting crude tall oil, comprising fatty acids, rosin acids and sterols, to the following steps:
   (a) esterifying said CTO with lower alcohols, wherein said fatty acids present in said CTO react selectively with the lower alcohols and removing lower alcohols and water from the esterified CTO mixture, forming a first CTO mixture comprising fatty acid lower alkyl esters;
   (b) transesterifying said first CTO mixture with said fatty acid lower alkyl esters in the presence of a transesterification catalyst to transform all free sterols into sterol fatty acid esters, forming a second CTO mixture comprising sterol fatty acid esters, which sterol fatty acid esters are less volatile and more thermally stable than the starting sterols;
   (c) separating said second CTO mixture into two fractions by short pass distillation, a first fraction comprising said fatty acid lower alkyl esters and said rosin acids, and a second fraction comprising said sterol esters of fatty acids;
   (d) further separating said first fraction into fatty acid alkyl esters and rosin acids in a process consisting essentially of short pass distillation or wiped film evaporator distillation; and
   (e) converting said sterol esters of fatty acids into the free sterols,
wherein step (a) is carried out in the liquid phase, optionally under pressure.

8. The process according to claim 7, wherein step (b) is conducted at a temperature in the range of 200 to 230° C.

9. The process according claim 1, wherein the separations of steps (c) and (d) are carried out by means of a wiped film evaporator or a fractionation column.

10. The process according to claim 9, wherein a wiped film evaporator is used, operating at a reduced pressure ranging from 0.01 to 10 mm/HG and a temperature in the range of 190 to 240° C.

11. The process according to claim 9, wherein a fractionation column is used, operating at a pressure ranging from 0.1 to 5 mmHG, and a temperature in the range of 170 to 230° C. at the top of said column and 240 to 280° C. at the bottom of said column.

12. The process according to claim 1, wherein the fatty acid alkyl esters of step (d) are substantially free of rosin acids.

13. The process according to claim 1, wherein the conversion of the sterol borates to free sterols of step (e) is effected by hydrolysis.

14. The process according to claim 7, wherein the conversion of the sterol esters of fatty acids to free sterols of step (e) is effected by solvolysis.

15. The process according to claim 14, wherein the solvolysis solvent comprises a polyol.

16. The process according to claim 7, wherein step (b) comprises transesterification in the presence of a tin catalyst.

17. The process according to claim 7, wherein said esterification step (a) is carried out in the presence of an acid catalyst or in the presence of an enzyme catalyst.

18. The process according to claim 17, wherein said esterification is carried out in the presence of an immobilized enzyme catalyst.

19. The process according to claim 7, wherein the separations of steps (c) and (d) are carried out by means of a wiped film evaporator or a fractionation column.

20. The process according to claim 19, wherein a wiped film evaporator is used, operating at a reduced pressure ranging from 0.01 to 10 mm/HG and a temperature in the range of 190 to 240° C., or a fractionation column is used, operating at a pressure ranging from 0.1 to 5 mmHG, and a temperature in the range of 170 to 230° C. at the top of said column and 240 to 280° C. at the bottom of said column.

\* \* \* \* \*